United States Patent
Leijssen et al.

(10) Patent No.: US 10,682,117 B2
(45) Date of Patent: Jun. 16, 2020

(54) STETHOSCOPE APPARATUS AND A METHOD OF PROCESSING BREATHING SOUNDS PRODUCED BY A SUBJECT

(71) Applicant: KONINKLIJKE PHILIPS N.V., Eindhoven (NL)

(72) Inventors: Jacobus Josephus Leijssen, Waalre (NL); Gerardus Johannes Nicolaas Doodeman, Veldhoven (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/475,313

(22) PCT Filed: Jan. 4, 2018

(86) PCT No.: PCT/EP2018/050157
§ 371 (c)(1),
(2) Date: Jul. 1, 2019

(87) PCT Pub. No.: WO2018/127524
PCT Pub. Date: Jul. 12, 2018

(65) Prior Publication Data
US 2019/0328352 A1  Oct. 31, 2019

(30) Foreign Application Priority Data
Jan. 9, 2017 (EP) .................... 17150641

(51) Int. Cl.
*A61B 7/00* (2006.01)
*A61B 5/00* (2006.01)
(Continued)

(52) U.S. Cl.
CPC .......... *A61B 7/003* (2013.01); *A61B 5/04007* (2013.01); *A61B 5/0816* (2013.01);
(Continued)

(58) Field of Classification Search
CPC .... H04R 1/46; H04R 3/00; H04R 3/12; A61B 5/05; A61B 5/04005; A61B 5/04007;
(Continued)

(56) References Cited

U.S. PATENT DOCUMENTS 5,812,678 A     9/1998  Davis
2001/0030077 A1* 10/2001  Watson .................. A61B 5/044
                                              181/131
(Continued)

FOREIGN PATENT DOCUMENTS

KR    2009070294 A    7/2009
WO    2006111877 A1   10/2006
(Continued)

OTHER PUBLICATIONS

International Search Report and Written Opinion, International Application No. PCT/EP2018/050157, dated Apr. 17, 2018.
(Continued)

*Primary Examiner* — Thang V Tran

(57) ABSTRACT

According to an aspect, there is provided a stethoscope apparatus stethoscope apparatus, the stethoscope apparatus comprising a sound sensor for measuring sounds produced by the breathing of a subject and for outputting a sound signal representing the measured breathing sounds; an antenna for receiving a modulated electromagnetic signal from the body, wherein the modulated electromagnetic signal is modulated by movement of air, fluid and/or tissue in the body; a processing unit that is configured to receive the sound signal from the sound sensor and the modulated electromagnetic signal from the antenna; and normalise the sound signal using the modulated electromagnetic signal.

14 Claims, 8 Drawing Sheets

(51) Int. Cl.
*H04R 3/00* (2006.01)
*A61B 5/04* (2006.01)
*A61B 5/08* (2006.01)
*H01Q 1/52* (2006.01)
*H01Q 7/06* (2006.01)
*A61B 7/02* (2006.01)
*A61B 5/05* (2006.01)
*G01R 29/08* (2006.01)

(52) U.S. Cl.
CPC .......... *A61B 5/7203* (2013.01); *A61B 5/7225* (2013.01); *A61B 7/02* (2013.01); *H01Q 1/526* (2013.01); *H01Q 7/06* (2013.01); *A61B 5/05* (2013.01); *A61B 2560/0462* (2013.01); *A61B 2562/0223* (2013.01); *A61B 2562/182* (2013.01); *A61B 2562/222* (2013.01); *G01R 29/0878* (2013.01); *H04R 3/00* (2013.01)

(58) Field of Classification Search
CPC ... A61B 5/0816; A61B 5/7203; A61B 5/7225; A61B 7/00; A61B 7/02; A61B 7/026; A61B 7/04; A61B 7/003; A61B 2562/0223; A61B 2562/0204; A61B 2562/166; A61B 2562/182; A61B 2562/222; A61B 2560/0462; G01R 29/0878; H01Q 1/526; H01Q 7/06
See application file for complete search history.

(56) References Cited

U.S. PATENT DOCUMENTS

2004/0228494 A1* 11/2004 Smith ...................... A61B 7/04 381/67
2005/0073424 A1 4/2005 Ruoss et al.
2008/0091239 A1* 4/2008 Johansson .......... A61N 1/36514 607/4
2009/0211838 A1* 8/2009 Bilan ...................... A61B 7/04 181/131
2010/0125218 A1* 5/2010 Haartsen ............ A61B 5/02438 600/528
2012/0302920 A1 11/2012 Bridger et al.
2014/0163343 A1 6/2014 Heneghan et al.
2016/0143557 A1 5/2016 Kahlman et al.
2018/0049716 A1* 2/2018 Rajagopal ............ A61B 5/7257
2018/0143150 A1 5/2018 Bezemer et al.

FOREIGN PATENT DOCUMENTS

WO 2016084473 A1 6/2016
WO 2016166318 A1 10/2016
WO 2017157989 A1 9/2017
WO 2018019648 A1 2/2018

OTHER PUBLICATIONS

Hamsch, M. et al., "Monitoring device for monitoring a physiological parameter of a subject", Jan. 2016, EP16153320.3.

Teichmann, D. et al., "Noncontact Monitoring of Cardiorespiratory Activity by Electromagnetic Coupling", IEEE Transactions on Biomedical Engineering, vol. 60, No. 8, Aug. 2013.

Gürsoy, D. et al., "Magnetic induction pneumography: a planar coil system for continuous monitoring of lung function via contactless measurements", Journal of Electrical Bioimpedance, 2010.

* cited by examiner

STETHOSCOPE APPARATUS AND A METHOD OF PROCESSING BREATHING SOUNDS PRODUCED BY A SUBJECT

CROSS-REFERENCE TO PRIOR APPLICATIONS

This application is the U.S. National Phase application under 35 U.S.C. § 371 of International Application No. PCT/EP2018/050157, filed on 4 Jan. 2018, which claims the benefit of European Patent Application No. 17150641.3, filed on 9 Jan. 2017. These applications are hereby incorporated by reference herein.

TECHNICAL FIELD OF THE INVENTION

The invention relates to an improved stethoscope apparatus that is for use in measuring the sounds of breathing by a subject.

BACKGROUND TO THE INVENTION

The stethoscope is one of the most commonly used medical instruments, and is often used by a doctor to listen to heart sounds and the sounds produced by the breathing of a subject. The stethoscope typically comprises a small receiver (e.g. a bell or diaphragm) that is placed against the subject's body and hollow tubes that transmit the sound detected by the receiver to the ears of the user.

Electronic stethoscopes are available that use a microphone to record the sounds inside the body, with the sounds being output to the user via a speaker.

Typically, when using a stethoscope a subject is required to breathe as deeply as possible to ensure that the breathing sounds are audible to a user of the stethoscope. However, some subjects may not be able to take sufficiently deep breaths, particularly those subjects that are unwell with a condition that affects their breathing.

There is therefore a need for an improved stethoscope apparatus and method of processing breathing sounds that addresses this problem.

SUMMARY OF THE INVENTION

According to a first aspect, there is provided a stethoscope apparatus, the stethoscope apparatus comprising a sound sensor for measuring sounds produced by the breathing of a subject and for outputting a sound signal representing the measured breathing sounds; a transmitting antenna for emitting an electromagnetic signal into the body; an antenna for receiving a modulated electromagnetic signal in response to the electromagnetic signal from the body, wherein the modulated electromagnetic signal is modulated by movement of air, fluid and/or tissue in the body; a processing unit that is configured to receive the sound signal from the sound sensor and the modulated electromagnetic signal from the antenna; and normalise the sound signal using the modulated electromagnetic signal. Normalising the sound signal makes anomalies more audible compared with just a standard audio stethoscope.

In some embodiments, the processing unit is configured to normalise the sound signal by dividing the amplitude of the measured sounds in the received sound signal by the amplitude of the modulated electromagnetic signal.

In some embodiments, the received sound signal comprises measurements of the amplitude of the sound at a plurality of sampling times, and the processing unit is configured to normalise the sound signal by dividing the amplitude of the measured sound at a particular sampling time by the amplitude of the modulated electromagnetic signal at said particular sampling time.

In some embodiments, the processing unit is configured to normalise the sound signal by analysing the modulated electromagnetic signal to estimate the volume of air inhaled and/or exhaled by the subject in each breath; and normalising the sound signal using the estimated volume of air inhaled and/or exhaled by the subject in each breath.

In some embodiments, the stethoscope apparatus further comprises a speaker for outputting the normalised sound signal to a user of the stethoscope apparatus.

In alternative embodiments, the transmitting antenna used for emitting the electromagnetic signal into the body is the same antenna, which is used for receiving the modulated electromagnetic signal.

According to a second aspect, there is provided a method of processing breathing sounds produced by a subject, the method comprising emitting an excitation electromagnetic signal into a body of the subject; measuring sounds produced by the breathing of a subject using a sound sensor and outputting a sound signal representing the measured breathing sounds; receiving a modulated electromagnetic signal from the body using an antenna, the modulated electromagnetic signal is modulated by movement of air, fluid and/or tissue in the body; and normalising the sound signal using the modulated electromagnetic signal. Normalising the sound signal makes anomalies more audible compared with just a standard audio stethoscope.

In some embodiments, the step of normalising the sound signal comprises dividing the amplitude of the measured sounds in the received sound signal by the amplitude of the modulated electromagnetic signal.

In some embodiments, the received sound signal comprises measurements of the amplitude of the sound at a plurality of sampling times, and the step of normalising the sound signal comprises dividing the amplitude of the measured sound at a particular sampling time by the amplitude of the modulated electromagnetic signal at said particular sampling time.

In some embodiments, the step of normalising the sound signal comprises analysing the modulated electromagnetic signal to estimate the volume of air inhaled and/or exhaled by the subject in each breath; and normalising the sound signal using the estimated volume of air inhaled and/or exhaled by the subject in each breath.

In some embodiments, the method further comprises outputting the normalised sound signal using a speaker.

In some embodiments, emitting of the electromagnetic signal into the body is performed using the antenna, which is also used for receiving the modulated electromagnetic signal. In alternative embodiments, emitting of the electromagnetic signal into the body is performed using a second (transmitting) antenna.

According to a third aspect, there is provided a computer program product comprising a computer readable medium having computer readable code embodied therein, the computer readable code being configured such that, on execution by a suitable computer or processor, the computer or processor is caused to perform any of the methods described above.

Thus, the normalisation according to the invention provides that audible breathing sounds can be obtained for a subject, regardless of the depth with which the subject is breathing or is able to breathe.

BRIEF DESCRIPTION OF THE DRAWINGS

Exemplary embodiments of the invention will now be described, by way of example only, with reference to the following drawings, in which.

DETAILED DESCRIPTION OF EMBODIMENTS

As noted above, when using a conventional acoustic stethoscope a subject is required to breathe as deeply as possible to ensure that the breathing sounds are audible to a user of the stethoscope (i.e. a physician or other healthcare provider). However, this can be difficult for some subjects since they may not be able to take sufficiently deep breaths and therefore it may be difficult for certain breathing sounds to be audible to the user of the stethoscope. Thus, the invention provides that information contained in an electromagnetic signal that is modulated by air, fluid and/or tissue movements in the body of the subject (and specifically breathing movements) can be used to normalise the sound of the subject's breathing. In particular, the modulations in the electromagnetic signal are related to the depth with which the subject is breathing, and thus this information is used to normalise the sound of the subject's breathing for the depth of the breathing.

Figure 1:
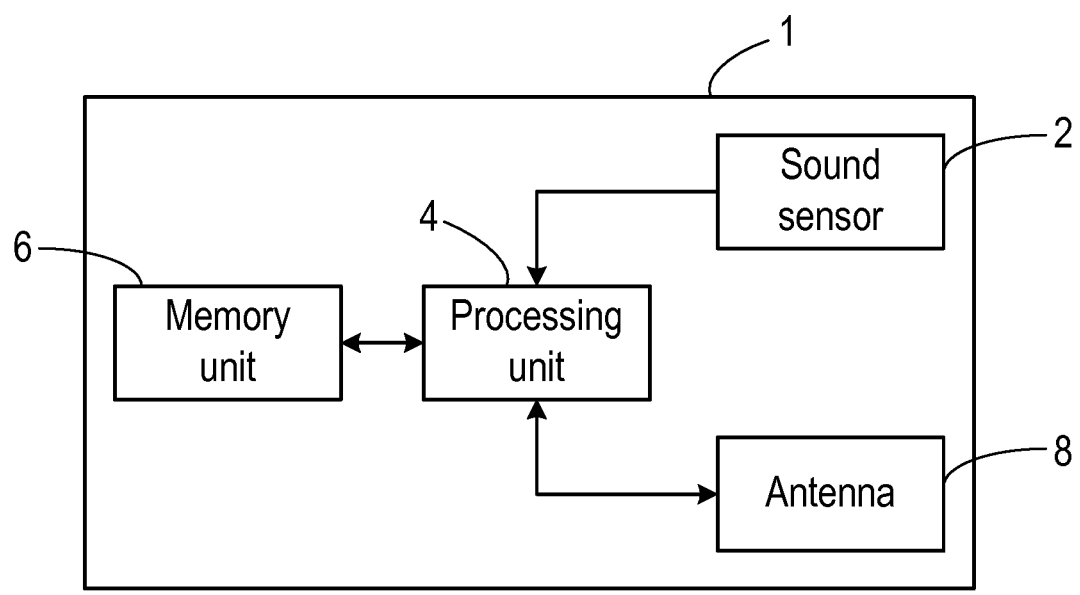
FIG. 1 is a block diagram of an apparatus according to an embodiment.
Figure 2:
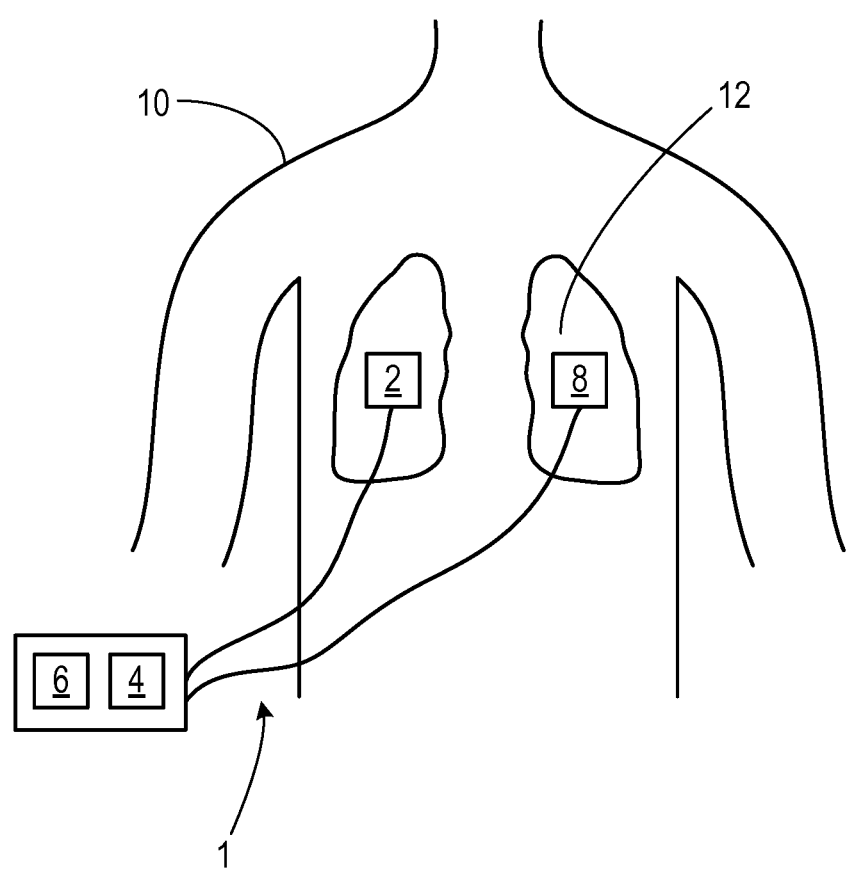
FIG. 2 is a block diagram of an apparatus in use on a subject.

An embodiment of a stethoscope apparatus 1 according to the invention is shown in FIG. 1. FIG. 2 shows the stethoscope apparatus 1 of FIG. 1 in use on a subject. The stethoscope apparatus 1 comprises a sound sensor 2 that is for measuring the sound of the breathing of a subject. The sound sensor 2 can comprise a microphone, multiple microphones, or any other type of sensor, for example an accelerometer, that can measure the sound of a subject breathing. The sound sensor 2 outputs a signal representing the measured sound. The sound signal can be an analog signal or a digital signal (i.e. comprising a measurement of the amplitude of the sound at each of a plurality of sampling instants). In the case of a digital signal, the sampling frequency of the sound sensor 2 can have any desired value. For example the sampling frequency can be 1 kiloHertz (kHz), or if oversampling is used to obtain additional data, the sampling frequency can be 22 kHz, 44.1 kHz (which is a standard audio sampling rate) or even higher.

The sound sensor 2 is connected to a processing unit 4 in the stethoscope apparatus 1, and the sound signal is provided to the processing unit 4.

The processing unit 4 generally controls the operation of the stethoscope apparatus 1, for example controlling the initiation of the recording of the sound signal by the sound sensor 2, and/or other functions and operations of the stethoscope apparatus 1, such as the processing of the sound signal according to the invention. The processing unit 4 can be implemented in numerous ways, with software and/or hardware, to perform the various functions required. The processing unit 4 may comprise one or more microprocessors that may be programmed using software to perform the required functions. The processing unit 4 may be implemented as a combination of dedicated hardware to perform some functions and a processor (e.g., one or more programmed microprocessors and associated circuitry) to perform other functions. Examples of processing components that may be employed in various embodiments of the present disclosure include, but are not limited to, conventional microprocessors, application specific integrated circuits (ASICs), and field-programmable gate arrays (FPGAs).

In various implementations, the processing unit 4 may be associated with one or more storage media, shown as memory unit 6 in FIG. 1. The memory unit 6 can be part of the processing unit 4, or it can be a separate component in the stethoscope apparatus 1 that is connected to the processing unit 4 (as shown in FIG. 1). The memory unit 6 can comprise any suitable or desired type of volatile or non-volatile computer memory such as RAM, PROM, EPROM, and EEPROM. The memory unit 6 can be used for storing computer program code that can be executed by the processing unit 4 to perform the method described herein. The memory unit 6 can also be used to store sound signals or measurements from the sound sensor 2 and/or any other sensors in the stethoscope apparatus 1, and/or information derived from the sound signals or other sensor measurements determined by the processing unit 4.

The stethoscope apparatus 1 also comprises an antenna 8 that is used to receive an electromagnetic signal from the body of the subject that has been modulated by movements of air, fluid and/or tissue in the body (e.g. caused by breathing and the beating of the heart). It will be appreciated that movements of tissue in the body can comprise changes in volume of the tissue. These modulations cause amplitude and/or phase modulations of the electromagnetic signal. The electromagnetic signal received by the antenna 8 is referred to herein as the modulated electromagnetic signal.

The modulated electromagnetic signal is emitted by the body in response to an excitation electromagnetic signal that is emitted into the body of the subject. The excitation electromagnetic signal causes magnetic induction, i.e. the generation of eddy currents in the tissue due to the application of an external magnetic field, and this eddy current/electromagnetic signal is modulated by the movements of air, fluid and/or tissue in the subject.

The excitation electromagnetic signal can be emitted either by the antenna 8 or by a separate transmitting antenna. This excitation electromagnetic signal can be emitted in response to an excitation signal provided from the processing unit 4 or from separate excitation circuitry (not shown in FIG. 1) that is controlled by the processing unit 4. In other words the antenna 8 can be also the transmitting antenna by performing both functions: emitting the electromagnetic signal into the body and receiving the modulated electromagnetic signal from the body in response to the excitation signal.

The emitted excitation electromagnetic signal (and thus the received modulated electromagnetic signal) can be a radio frequency (RF) signal, for example with a frequency of the order of hundreds of megahertz (MHz), for example a frequency in the range of 100 MHz to 1000 MHz. In a specific example, the antenna 8 can be configured to receive an electromagnetic signal with a frequency of 450 MHz.

Magnetic fields penetrate deeper into a body than electrical fields, and thus magnetic fields can be used to measure changes in properties deeper inside the body, whereas electrical fields can be used to measure changes in properties on the surface of the skin, e.g. the permittivity of the skin. Thus, the antenna 8 is preferably configured such that it is a magnetic antenna, i.e. such that the magnetic field behaviour of the emitted electromagnetic signal dominates over the electric field behaviour.

Preferably the antenna 8 is small compared to the wavelength of the electromagnetic signal that the antenna 8 is to measure for the loop to be considered as a magnetic antenna. In some embodiments, the diameter of a loop antenna can be considered to be small if it is less than 10% of the wavelength of the electromagnetic signal.

In some embodiments, which are described in more detail below with reference to FIG. 3, the antenna 8 comprises a loop antenna. In some of these embodiments, the loop antenna is shielded with a Faraday shield to lower the electrical field (the near field). In alternative embodiments, the antenna 8 is a coil antenna.

In some embodiments, all of the components of the stethoscope apparatus 1 are part of the same device, e.g. the sound sensor 2, processing unit 4 and antenna 8 are in a single housing. In other embodiments the sound sensor 2 and/or antenna 8 are in a separate device or housing to the processing unit 4. Where the sound sensor 2 and/or antenna 8 are provided in a separate device or housing to the processing unit 4, appropriate circuitry or components can be provided to enable the sound signal and/or received modulated electromagnetic signal to be sent (e.g. transmitted) to the processing unit 4. In these cases the processing unit 4 can be part of a personal electronic device such as a smartphone, tablet computer, laptop computer or desktop computer, or part of another electronic device, such as a base unit or hub unit for the sound sensor 2 and/or antenna 8, or a remote server (e.g. located in the cloud, i.e. accessible via the Internet), in which case the measurements from the sound sensor 2 and/or antenna 8 can be sent wirelessly to the processing unit 4 in the electronic device using any suitable communication protocol (e.g. Wi-Fi, Bluetooth, or a cellular telecommunication protocol).

In some embodiments the processing unit 4 can receive the sound signal from the sound sensor 2 and modulated electromagnetic signal from the antenna 8 in real-time or near real-time (e.g. with the only delay being due to the signal processing required to transmit or convey the measurements to the processing unit 4). In other embodiments (including embodiments where the sound sensor 2 and/or antenna 8 are separate from the processing unit 4, the sound signal and modulated electromagnetic signal can be stored in memory unit 6 and the processing unit 4 can retrieve a previously-obtained sound signal from the memory unit 6 when a sound signal is to be analysed or processed.

As noted above, in some embodiments the processing unit 6 may be part of a smartphone or other general purpose computing device that can be connected to or otherwise receive a sound signal from a sound sensor 2 and/or modulated electromagnetic signal from the antenna 8, but in other embodiments the stethoscope apparatus 1 can be an apparatus that is dedicated to the purpose of obtaining and processing a sound signal.

It will be appreciated that FIG. 1 only shows the components required to illustrate various embodiments of the stethoscope apparatus 1, and in a practical implementation the stethoscope apparatus 1 may comprise additional components to those shown. For example, the stethoscope apparatus 1 may comprise a battery or other power supply for powering the stethoscope apparatus 1, a communication module for enabling the processed sound signal to be communicated to another device, e.g. a base unit for the stethoscope apparatus 1 or a remote computer, and/or one or more user interface components. As an example, the one or more user interface components could comprise a switch, a button or other control means for activating and deactivating the stethoscope apparatus 1 and/or sound signal processing. The user interface components can also or alternatively comprise a speaker for outputting the processed sound signal and/or a display or other visual indicator for displaying a graphical representation of the processed sound signal.

FIG. 2 shows the stethoscope apparatus 1 of FIG. 1 in use on a subject 10. In particular, the sound sensor 2 and antenna 8 are placed on the chest or back of the subject 10, in the vicinity of the lungs 12 of the subject 10. The sound sensor 2 can therefore measure the sound of the breathing by the subject 10 (and also the sound of the heart beating), and the antenna 8 can receive an electromagnetic signal that has been modulated by the movement of the lungs (breathing) and/or heart (heart beats).

It will be appreciated that in some embodiments the sound sensor 2 and antenna 8 can be in the same unit and therefore may be in the same location on the body of the subject 10.

Figure 3:
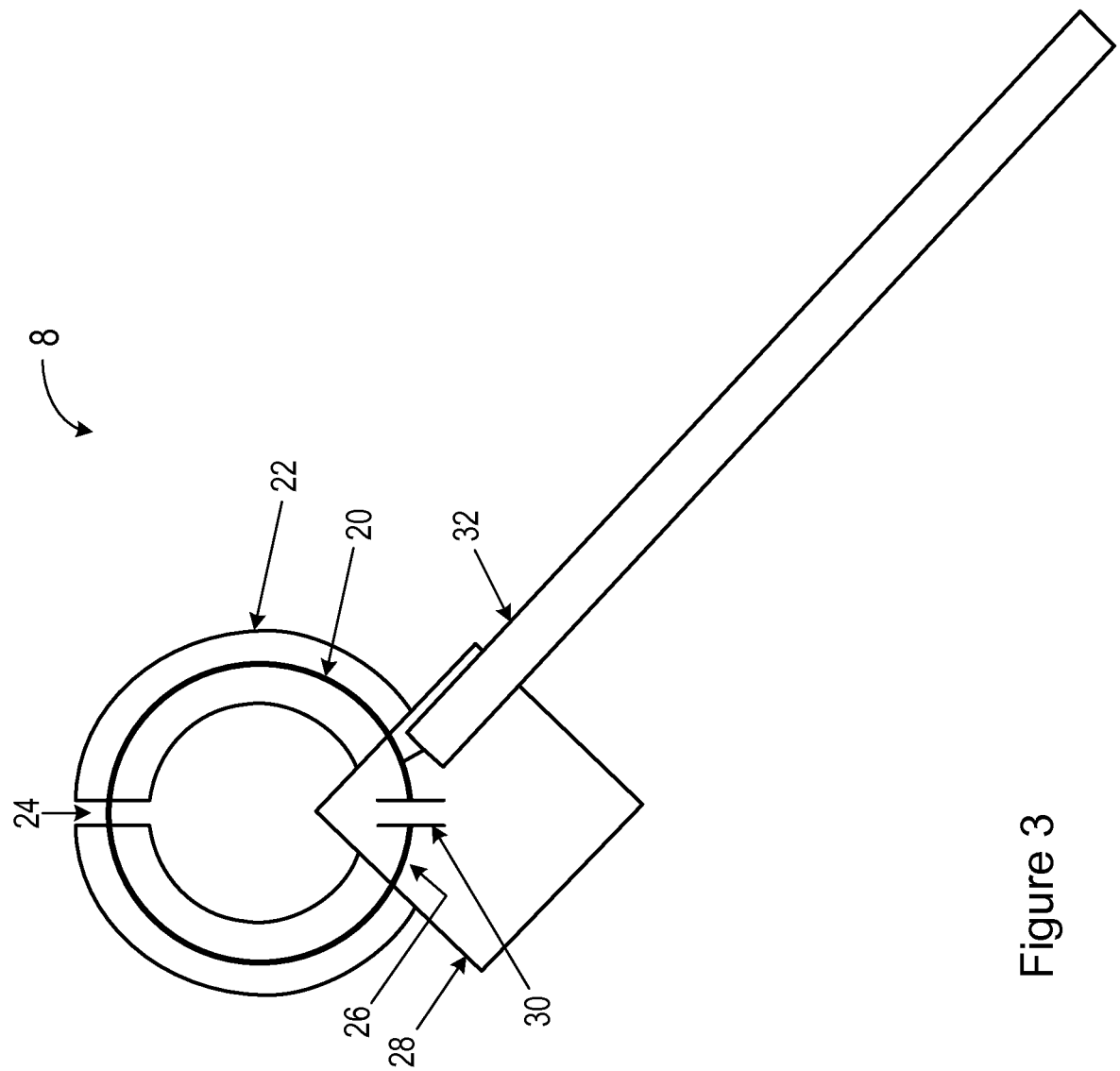
FIG. 3 is a diagram of an antenna according to an exemplary embodiment.

FIG. 3 shows an exemplary antenna 8 according to an embodiment. The antenna 8 comprises a radiating element in the form of a wire loop 20 that is shielded across its length by a first shielding component 22, except at an opening 24 where the wire loop 20 is exposed and at a part 26 that is located inside a second shielding component 28. This opening 24 is required to prevent shorting of the antenna 8.

The second shielding component 28 covers the part 26 of the wire loop 20, and can be made of metal to act as a Faraday shield.

A capacitor 30 is connected to the part 26 of the wire loop 20 that is located inside the second shielding component 28. The capacitor 30 is provided for tuning the antenna 8.

A cable 32 is connected at one end to the wire loop 20 inside the second shielding component 28 and allows any signal received by the wire loop 20 to be output to the processing unit 4. Where the antenna 8 is also used to emit the excitation electromagnetic signal, the cable 32 can be used to provide the excitation signal from the processing unit 4 to the wire loop 20.

In some embodiments, the antenna 8 can also include an electrostatic discharge (ESD) shield to lower the electrical field residue. This ESD shield could be formed from a metallic non-conducting foil.

In practical embodiments, the wire loop 20 and first shielding component 22 can be a coaxial cable that is formed into a circular shape, with the inner conductor of the coaxial cable acting as the wire loop 20 and the outer part of the coaxial cable acting as the shield (Faraday shield). In alternative embodiments, the antenna 8 can be formed using two layers of PCB (printed circuit board) material that act as a Faraday shield.

As noted above the diameter of the antenna 8 is preferably small compared to the wavelength of the electromagnetic signal (in air) that the antenna 8 is to measure. Thus, for an antenna 8 that is to receive signals at 450 MHz (with a wavelength of 0.66 metres (m)), the wire loop 20 can have a diameter of 15 millimetres (mm). In another example, for an antenna 8 that is to receive signals at 118 MHz, the wire loop 20 can have a diameter of 45 mm.

It has been found that with the antenna 8 of FIG. 3, at higher frequencies, e.g. around 1000 MHz, changes in phase of the received signal dominate the changes in amplitude of the received signal due to motion of air/tissue/fluid in the body of the subject. At lower frequencies, e.g. around 100 MHz, the amplitude changes will dominate the changes in phase.

Those skilled in the art will appreciate that the antenna 8 shown in FIG. 3 is merely exemplary, and other types of antenna 8 can be used.

The antenna 8 can be used in several ways to obtain the modulated electromagnetic signal. Two exemplary embodiments are described below, but it should be appreciated that other arrangements are possible. In a first embodiment, the antenna 8 can be used to receive an electromagnetic signal at a resonance frequency of the antenna 8 and the modulated electromagnetic signal is a measurement of the return loss of the antenna. Those skilled in the art will be aware of techniques for measuring the return loss of an antenna 8 and further details are not provided herein. The processing unit 4 can be configured to measure changes in frequency, amplitude and/or phase of the modulated electromagnetic signal.

For a loop antenna 8 as shown in FIG. 3, the loop resonates at two frequencies, an inner loop resonance and outer loop resonance. That is, the inner loop 20, which is shielded by the outer loop (the shielding component 22), is used as the measurement antenna and has an inner loop resonance. The shield acts as a loop as well (it is parasitic) with its own higher resonance frequency. Thus, the loop has two resonance frequencies and the lowest is used.

Figure 4:
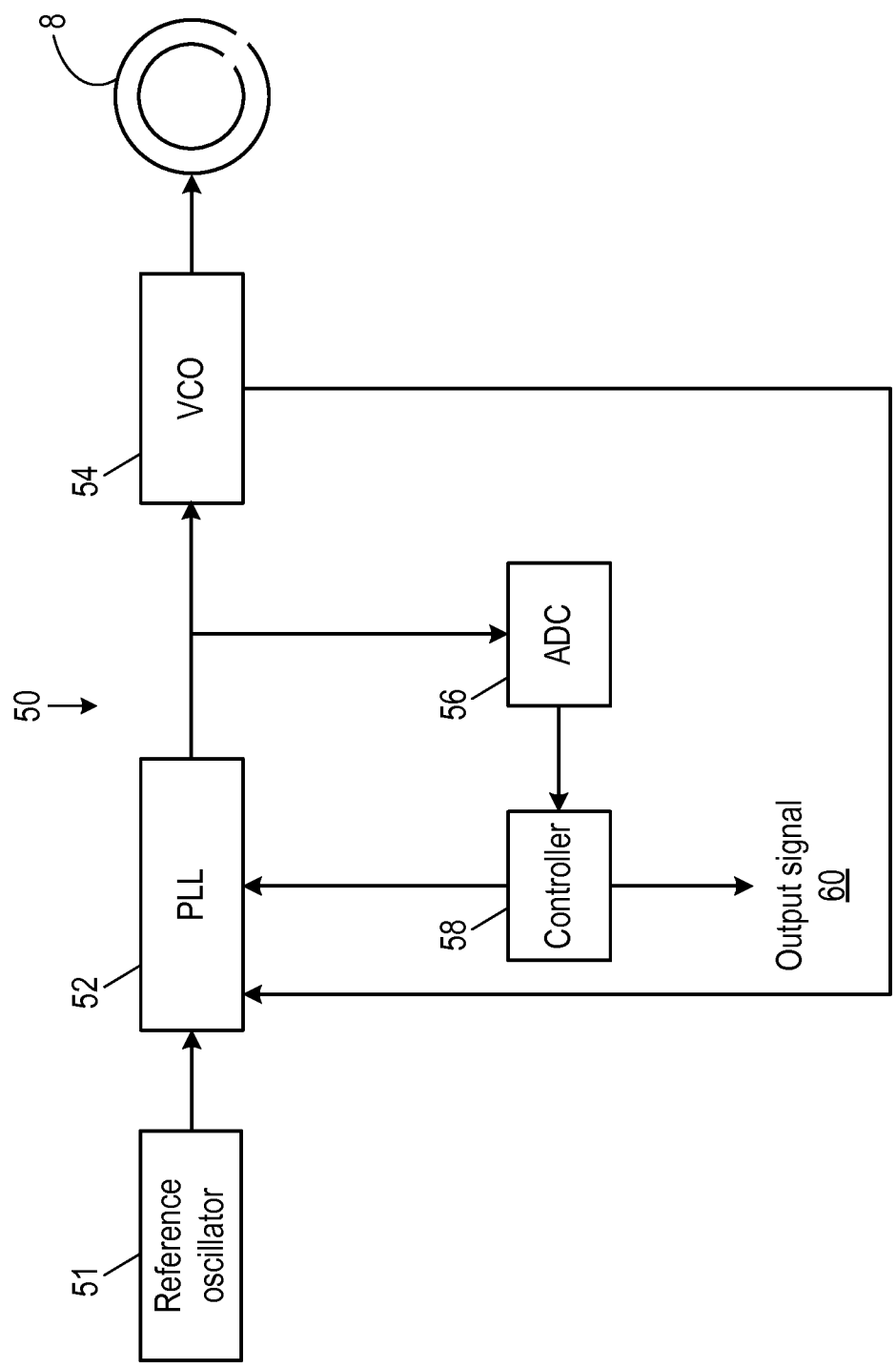
FIG. 4 is block diagram of control circuitry for obtaining an electromagnetic signal from an antenna.

A second embodiment is shown in FIG. 4. In this embodiment a phase locked loop (PLL) is used to generate the excitation signal for the antenna 8, and the control signal for the PLL provides the output signal representing the movement of air, fluid and/or tissue in the body of the subject.

FIG. 4 shows control circuitry 50 for the antenna 8, and comprises a reference oscillator 51, a PLL 52 that is connected to the reference oscillator 51 and that outputs an analog control signal (known as $V_{tune}$) to a voltage-controlled oscillator (VCO) 54. The $V_{tune}$ signal is a result of a comparison of the signal from the reference oscillator 51 to the signal from the VCO 54. In response to the PLL analog control signal the VCO 54 generates an excitation signal at a required frequency and provides this to the antenna 8 so that the antenna 8 emits the excitation electromagnetic signal. As noted above the excitation electromagnetic signal will induce eddy currents in the body of the subject, and these eddy currents will induce a current in the antenna 8.

The excitation signal is also provided to the PLL 52 as part of the feedback loop. The analog control signal from the PLL 52 is also provided to an analog-to-digital convertor (ADC) 56 which converts the analog control signal into a digital signal, and this digital signal is provided to a controller 58. The controller 58 determines a digital control signal for the PLL 52 and provides this to the PLL 52. As is known, in a PLL system, if the phase of the VCO 54 differs from the phase of the reference oscillator 51, the digital control signal corrects the VCO phase.

Movements of air, fluid and/or tissue in the body effectively detune the antenna 8, and the digital control signal counters this detuning and corrects the phase of the VCO 54. The digital control signal therefore carries the information on the movements of the air, fluid and/or tissue, and the controller 58 determines an output signal 60 from the digital control signal that represents or contains the information on the movements of air, fluid or tissue in the body of the subject. Although this output signal 60 does not carry the actual phase and amplitude information, the physiological characteristics (e.g. heart rate, breathing rate) are clearly observable.

The correction signal $V_{tune}$ that is required to keep the VCO 54 at the required frequency is used to measure amplitude and/or phase shifts due to movements of air, fluid and/or tissue in the body of the subject. The phase shifts tend to dominate the amplitude changes. The PLL correction signal (the digital control signal output by the controller 58 derived from the analog PLL correction signal 50) is used to determine the output signal 60. For example the output signal 60 can correspond to the digital control signal with suitable filtering and/or down-sampling to improve the signal-to-noise ratio.

Figure 5:
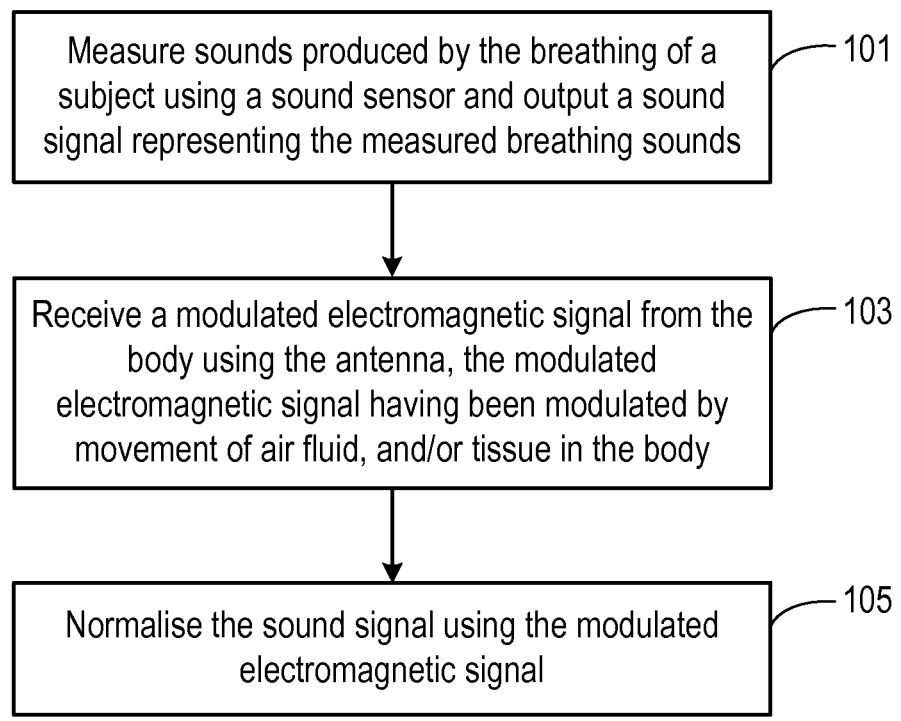
FIG. 5 is a flow chart illustrating a method of processing breathing sounds produced by a subject.

The flow chart in FIG. 5 illustrates a method of processing breathing sounds produced by a subject according to the invention.

Figure 6:
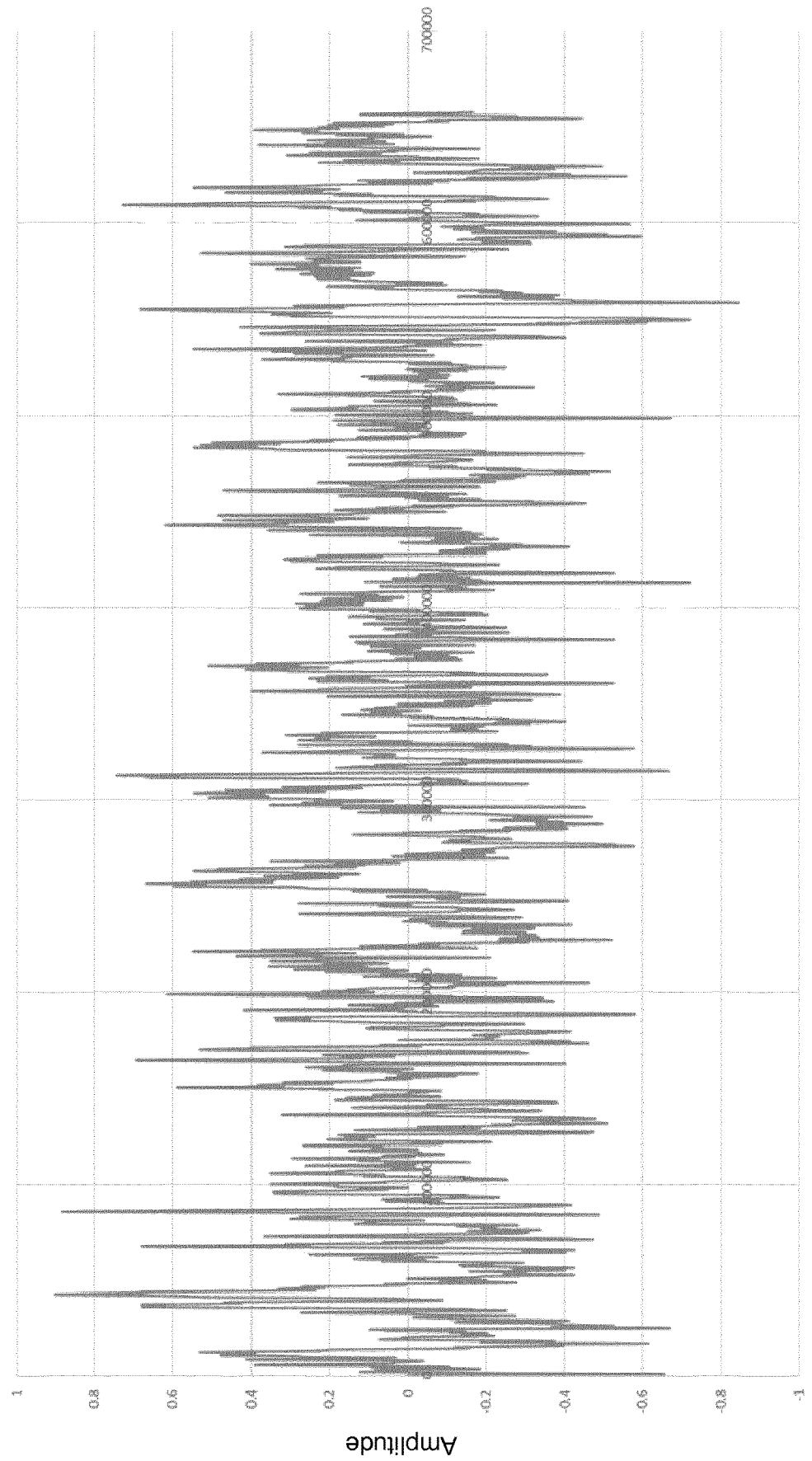
FIG. 6 is an exemplary sound signal.

In a first step, step 101, the sounds produced by the breathing of a subject 10 are measured. This step can be performed by a sound sensor 2 as described above, and the sound sensor 2 can output a sound signal representing the measured breathing sounds. It will be appreciated that the sound sensor 2 will also measure other sounds, such as the beating of the heart, and other sounds in the environment of the subject 10. The plot in FIG. 6 shows an exemplary sound signal obtained using an accelerometer. In some embodiments, the sound signal may be low pass filtered in order to remove parts of the signal relating to heart beats (and noise), which occur with a higher frequency than breaths. Thus, the low pass filtering may have a cut-off frequency that is between a typical heart rate and a typical breathing rate.

In a second step, step 103, which typically occurs at the same time as step 101 (i.e. at the same time that the sound signal is obtained), a modulated electromagnetic signal is received from the body using an antenna 8. This modulated electromagnetic signal will have been modulated by the movement of air, fluid and/or tissue in the body.

In some embodiments, the modulated electromagnetic signal can be filtered to remove or minimise noise.

In some embodiments, the method can further comprise a step of emitting an excitation electromagnetic signal into the body of the subject 10. This excitation electromagnetic signal can be emitted into the body of the subject 10 using the antenna 8, or a second antenna.

Figure 7:
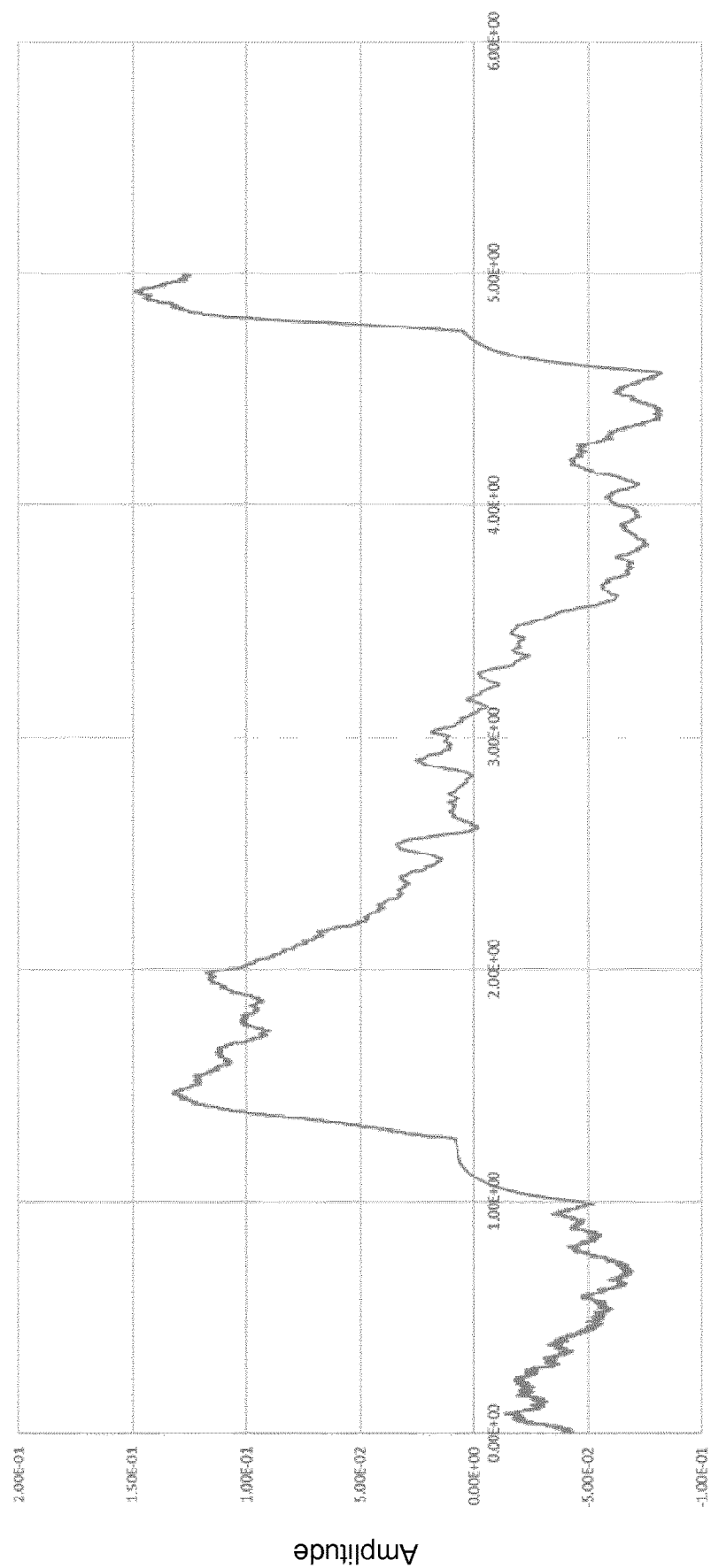
FIG. 7 is an exemplary breathing signal obtained using an antenna.

FIG. 7 shows an exemplary modulated electromagnetic signal obtained by an antenna 8 placed near a left-hand side rib of a subject for a 5-second period, and variations in the signal amplitude due to breathing can clearly be seen.

Figure 8:
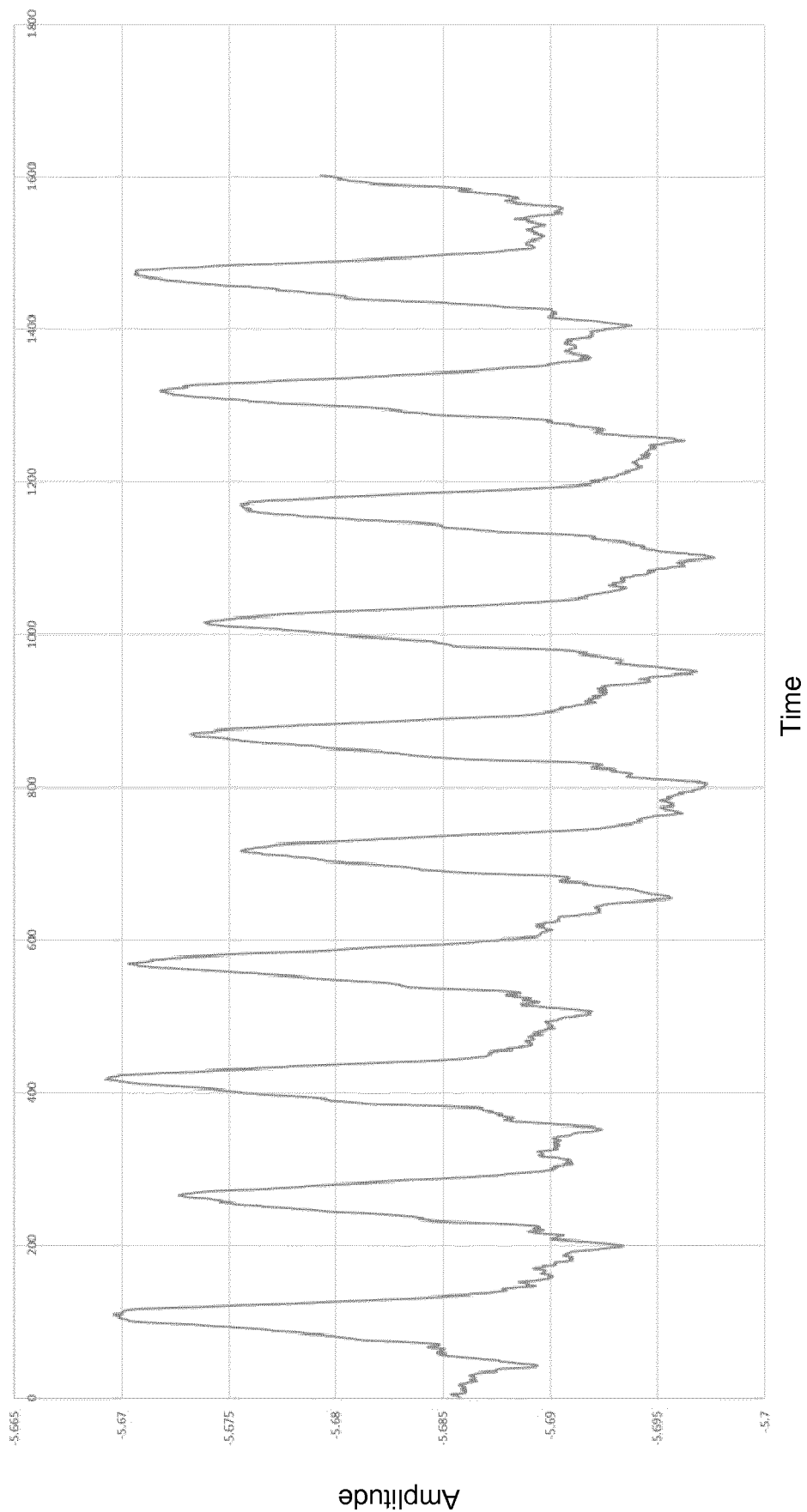
FIG. 8 shows the result of normalising a sound signal using the electromagnetic signal according to an embodiment.

Next, in step 105, the sound signal is normalised using the modulated electromagnetic signal. The modulations in the modulated electromagnetic signal are related to the depth with which the subject 10 is breathing (i.e. how much air is being inhaled and/or exhaled), and thus this information is used to normalise the sound of the subject's breathing for the depth of the breathing. FIG. 8 shows the result of normalising a sound signal using the electromagnetic signal according to an embodiment. In particular, FIG. 8 shows the result of normalising a sound signal that has been low-pass filtered to remove much of the signal relating to the heart beating. It will be appreciated that in FIG. 8 the time axis is drawn with a different scale to FIGS. 6 and 7.

In some embodiments, the normalised sound signal can be output to a user of the stethoscope apparatus 1, and thus the method can further comprise outputting the normalised sound signal to a user of the apparatus 1. For example the normalised sound signal can be output via a speaker in or associated with the apparatus 1. Alternatively or in addition, the normalised sound signal can be displayed graphically by a display screen on or associated with the apparatus 1.

In some embodiments, the sound signal is normalised by dividing the amplitude of the measured sounds in the sound signal by the amplitude of the modulated electromagnetic signal. That is, the sound signal will comprise measurements of the amplitude of the sound at a plurality of sampling times, and the sound signal is normalised by dividing the amplitude of the measured sound at a particular sampling time by the amplitude of the modulated electromagnetic signal at that time. Where the sound signal has been filtered in step 101, the filtered sound signal can be normalised in step 105.

Depending on the relative processing times of the sound signal and the electromagnetic signal, it may be useful or necessary to apply a time shift to one of the signals so that they are aligned in time before normalising the (possibly filtered) sound signal. This time-shifting will improve the visibility or audibility of the physiological characteristic in the normalised sound signal.

Alternatively, the modulated electromagnetic signal can be analysed to estimate the volume of air inhaled and/or exhaled by the subject in each breath, and the sound signal can be normalised using the estimated volume of air inhaled and/or exhaled.

Therefore, there is provided an improved stethoscope apparatus and method of processing breathing sounds.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other processing unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A stethoscope apparatus, the stethoscope apparatus comprising:
   a sound sensor for measuring sounds produced by the breathing of a subject and for outputting a sound signal representing the measured breathing sounds;
   a transmitting antenna for emitting an excitation electromagnetic signal into a body of the subject;
   an antenna for receiving a modulated electromagnetic signal from the body in response to the excitation electromagnetic signal, wherein the modulated electromagnetic signal is modulated by movement of air, fluid and/or tissue in the body;
   a processing unit that is configured to:
   receive the sound signal from the sound sensor and the modulated electromagnetic signal from the antenna; and
   normalise the sound signal using the modulated electromagnetic signal.

2. The stethoscope apparatus as claimed in claim 1, wherein the processing unit is configured to normalise the sound signal by:
   dividing an amplitude of the measured sounds in the received sound signal by an amplitude of the modulated electromagnetic signal.

3. The stethoscope apparatus as claimed in claim 2, wherein the received sound signal comprises measurements of the amplitude of the sound at a plurality of sampling times, and wherein the processing unit is configured to normalise the sound signal by:
   dividing the amplitude of the measured sound at a particular sampling time by the amplitude of the modulated electromagnetic signal at said particular sampling time.

4. The stethoscope apparatus as claimed in claim 1, wherein the processing unit is configured to normalise the sound signal by:
   analysing the modulated electromagnetic signal to estimate the volume of air inhaled and/or exhaled by the subject in each breath; and
   normalising the sound signal using the estimated volume of air inhaled and/or exhaled by the subject in each breath.

5. The stethoscope apparatus as claimed in claim 1, wherein the stethoscope apparatus further comprises:
   a speaker for outputting the normalised sound signal to a user of the stethoscope apparatus.

6. The stethoscope apparatus as claimed in claim 1, wherein the transmitting antenna is the same antenna as the antenna used for emitting the electromagnetic signal into the body.

7. A method of processing breathing sounds produced by a subject, the method comprising:
   measuring sounds produced by the breathing of a subject using a sound sensor and outputting a sound signal representing the measured breathing sounds;
   emitting an excitation electromagnetic signal into a body of the subject;
   receiving a modulated electromagnetic signal from the body in response to the excitation electromagnetic signal using an antenna, wherein the modulated electromagnetic signal is modulated by movement of air, fluid and/or tissue in the body; and
   normalising the sound signal using the modulated electromagnetic signal.

8. The method as claimed in claim 7, wherein the step of normalising the sound signal comprises:
   dividing an amplitude of the measured sounds in the received sound signal by an amplitude of the modulated electromagnetic signal.

9. The method as claimed in claim 8, wherein the received sound signal comprises measurements of the amplitude of the sound at a plurality of sampling times, and wherein the step of normalising the sound signal comprises:
   dividing the amplitude of the measured sound at a particular sampling time by the amplitude of the modulated electromagnetic signal at said particular sampling time.

10. The method as claimed in claim 9, wherein the step of normalising the sound signal comprises:

analysing the modulated electromagnetic signal to estimate the volume of air inhaled and/or exhaled by the subject in each breath; and normalising the sound signal using the estimated volume of air inhaled and/or exhaled by the subject in each breath.

11. The method as claimed in claim 7, wherein the method further comprises:

outputting the normalised sound signal using a speaker.

12. The method as claimed in claim 7, wherein emitting of the electromagnetic signal into the body is performed using the antenna, which is also used for receiving the modulated electromagnetic signal.

13. The method as claimed in claim 7, wherein emitting of the electromagnetic signal into the body is performed using a transmitting antenna.

14. A computer program product comprising a computer readable medium having computer readable code embodied therein, the computer readable code being configured such that, on execution by the processing unit of a stethoscope, the processing unit is caused to perform the method of claim 7.

\* \* \* \* \*